United States Patent [19]

McCue et al.

[11] Patent Number: 5,411,022
[45] Date of Patent: May 2, 1995

[54] CONTINUOUS PH MONITORING SYSTEM AND METHOD OF USING SAME

[76] Inventors: Michael McCue, 6015 Camino De La Acousta; Sam Z. Malhas, 6135 Waverly Ave., both of La Jolla, Calif. 92037; Don J. Cretzler, 3712 Del Mar Ave., San Diego, Calif. 92106; Richard A. Roshon, 2760 Lone Jack Rd., Olivenhaim, Calif. 92024

[21] Appl. No.: 85,769
[22] Filed: Jul. 1, 1993
[51] Int. Cl.⁶ ............................................. A61B 5/00
[52] U.S. Cl. .................................. 128/632; 128/635; 128/642; 128/780
[58] Field of Search ............... 128/632, 633, 634, 635, 128/636, 642, 747, 8, 716, 719, 772, 780, 773, 734, 696; 607/124

[56] References Cited

U.S. PATENT DOCUMENTS

| | | | |
|---|---|---|---|
| 3,373,735 | 3/1968 | Gallagher | 128/636 |
| 4,090,518 | 5/1978 | Elam | 128/696 X |
| 4,381,011 | 4/1983 | Somers, 3rd | 128/635 |
| 4,618,929 | 10/1986 | Miller et al. | 128/635 X |
| 4,632,119 | 12/1986 | Reichstein | 128/636 X |
| 4,718,423 | 1/1988 | Willis et al. | 128/634 |
| 4,774,956 | 10/1988 | Kruse et al. | 128/635 |
| 4,981,470 | 1/1991 | Bombeck, IV | 128/635 |
| 5,105,812 | 4/1992 | Gorman | 128/635 |
| 5,117,827 | 6/1992 | Stuebe et al. | 128/635 |

Primary Examiner—Lee S. Cohen
Assistant Examiner—Samuel Gilbert
Attorney, Agent, or Firm—Bernard L. Kleinke; Jerry R. Potts

[57] ABSTRACT

A continuous pH monitoring system and method of using it, includes a catheter assembly having a flexible compressible multipassagewayed tube, an anchor assembly connected to the tube to secure it within the nasal cavity, an indicator assembly having a sensor device within the tube to monitor the pH in the stomach, a vent within the tube to equalize pressure inside the stomach with the ambient pressure, and an aspirating assembly attached to the tube for removing stomach fluid.

10 Claims, 3 Drawing Sheets

CONTINUOUS PH MONITORING SYSTEM AND METHOD OF USING SAME

TECHNICAL FIELD

The present invention relates to a system and a method for continuously monitoring the pH in a patient's stomach using a nasogastric tube assembly and, more particularly, to such a system and method which minimizes the amount of patient discomfort.

BACKGROUND ART

The measurement of the pH level within the interior of the stomach has long been recognized as a method of diagnosis of a patient's condition. An early method for measuring the pH level included the insertion of a hollow tube into the patient's nose and through the esophagus to the stomach. Stomach fluids were then removed through the tube by aspiration and collected. Once collected, the fluids were tested for acidity.

In an attempt to measure the pH level of the stomach without using such a tube, an in vivo device which could be swallowed and subsequently removed for pH analysis was devised. Such a device is described in U.S. Pat. No. 3,528,429 issued to Beal et al. Described therein is a capsule containing coiled string which is coated with a pH indicator. One end of the string is held while the capsule is swallowed. The string is then removed, permitting a visual inspection of the pH indicator. While such a device was adequate for situations where the patient was in a noncritical condition and could cooperate in the process, it was not adequate for situations where the patient was suffering from shock, a condition which can be monitored by measuring intramuscosal pH in the stomach.

As discussed in an article by R. G. Riddian-Green et al. in Goals for the Resuscitation of Shock, *Critical Care Medicine* 1993, 21:525–531, the measurement of tissue pH provides an indication of the tissue oxygenation abilities of the patient. These abilities are especially important in determining whether a patient has been fully resuscitated from shock. Conventional methods for determining resuscitation from Shock, such as monitoring blood pressure, heart rate, cardiac output, hematocrit determinations, and blood gases, are not adequate for determining complete and optimal resuscitation.

Thus, Riddian-Green et al. proposed using an intraluminally located gastrointestinal tonometer for indirect measurement of intramuscosal pH in the stomach. The tonometer included a saline filled balloon which was placed in the stomach. $CO_2$ in the balloon saline then equilibrated with the mucosal $CO_2$. In this way, the tonometer provided a measurement of $PCO_2$ which was used with a simultaneous measurement of arterial carbonate in determining mucosal pH as calculated by the Henderson-Hasselbalch equation. Once the mucosal pH was calculated, a more complete picture of the patient's resuscitation from shock, was possible as the tissue oxygenation abilities were known.

Using a gastrointestinal tanometer of the type described in the Riddian-Green et al. article requires a nasogastric tube dedicated for such use. Where other operations, such as aspiration of the stomach, are to be performed in conjunction with the measurement of stomach pH, two or more nasogastric tubes are required. As the cross-sectional area of the nasogastric tract is limited, the use of two or more tubes is an inefficient method of utilizing the available area of the tract.

Thus, it would be highly-desirable to have an apparatus, and a method of using it, for performing multiple tasks relating to the gastrointestinal system, including the determination of the stomach pH. The apparatus, and method of using it, should utilize the available cross-sectional area in an efficient manner.

Such an apparatus, and the associated method, should include a nasogastric tube for providing unobstructed access to the stomach from outside of the patient's body which can perform many functions, thereby reducing patient discomfort by repeated insertion and removal of the tube. Multi-passagewayed tubes have been proposed in the past which could perform more than one function. These include the tubes described in U.S. Pat. Nos. 3,593,713; 4,280,501; 4,584,998; 4,735,607; 5,076,268 and 5,176,638.

All of the tube patents named above describe a somewhat rigid tube which does not conform easily to the nasogastric passage during insertion, causing great discomfort to the patient, and which are prone to being pinched down, blocking access to the stomach, at the 90 degree bend as the tube passes from the nasal cavity to the esophagus at the back of the throat.

U.S. Pat. No. 5,085,216 describes a tube which is completely collapsible for comfort. A stiffener, having a pH indicator attached thereto, is inserted into the tube for insertion. The pH indicator shows whether the tube has been correctly inserted. Once inserted, the stiffener and pH indicators are removed and the patient can then be fed. Although many functions can be performed by the tube, they cannot be done simultaneously.

Thus, it would also be desirable to have an apparatus, and method of using it, for continuously monitoring stomach pH which uses a partially collapsible nasogastric tube having multiple passageways and which can be inserted into the nasogastric tract without causing large amount of patient discomfort and which will not be closed off, blocking the passage between both ends of the tube.

Once the nasogastric tube is in place, it often happens that the patient is required to change positions. As a result of the position change, the tube is moved within the nasogastric passage, chaffing sensitive tissue within the nasal cavity. To prevent tube movement after the tube is inserted in previous tube arrangements, an inflatable balloon has been provided at the distal end of the tube to hold the end firmly in place. After the tube is inserted and the distal end is at the desired location, the balloon is inflated to expand outwardly, thereby pressing against the inner wall of the nasogastric tract. However, such an arrangement still permits the tube to move and rub against delicate nasal cavity tissue.

Thus, it would further be desirable to have such an apparatus, and a method of using it, which could be held in place to prevent movement of the tube within the nasal cavity.

DISCLOSURE OF INVENTION

Therefore, it is a principal object of the present invention to provide a new and improved continuous pH monitoring system and method of using it wherein the stomach pH of a patient can be determined directly as required, continuously, and without a blood gas laboratory.

Another object of the present invention is to provide such a new and improved continuous pH monitoring system and method of using it, such that the system uses a nasogastric tube capable of performing multiple functions simultaneously and which is partially collapsible to reduce patient discomfort during insertion yet will not block off communication between both ends of the tube.

A further object of the present invention is to provide such a new and improved continuous pH monitoring system and method of using it, such that any patient movement is not translated into discomfort to the patient from the tube rubbing sensitive tissue within the nasal cavity.

Briefly, the above and further objects of the present invention are realized by providing a continuous pH monitoring system and method of using it, such that the stomach pH of a patient can be directly measured on demand. The system utilizes a nasogastric tube capable of performing multiple functions simultaneously and which does not cause undue discomfort to the patient during insertion into the nasogastric tract. Once in place, movement by the patient will not result in the tube contacting and rubbing sensitive nasal cavity tissue, causing even more patient discomfort.

A continuous pH monitoring system and method of using it, includes a catheter assembly having a flexible compressible multipassagewayed tube, an anchor assembly connected to the tube to secure it within the nasal cavity, an indicator assembly having a sensor device within the tube to monitor the pH in the stomach, a vent within the tube to equalize pressure inside the stomach with the ambient pressure, and an aspirating assembly attached to the tube for removing stomach fluid.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein.

BEST MODE FOR CARRYING OUT THE INVENTION

Figure 1:
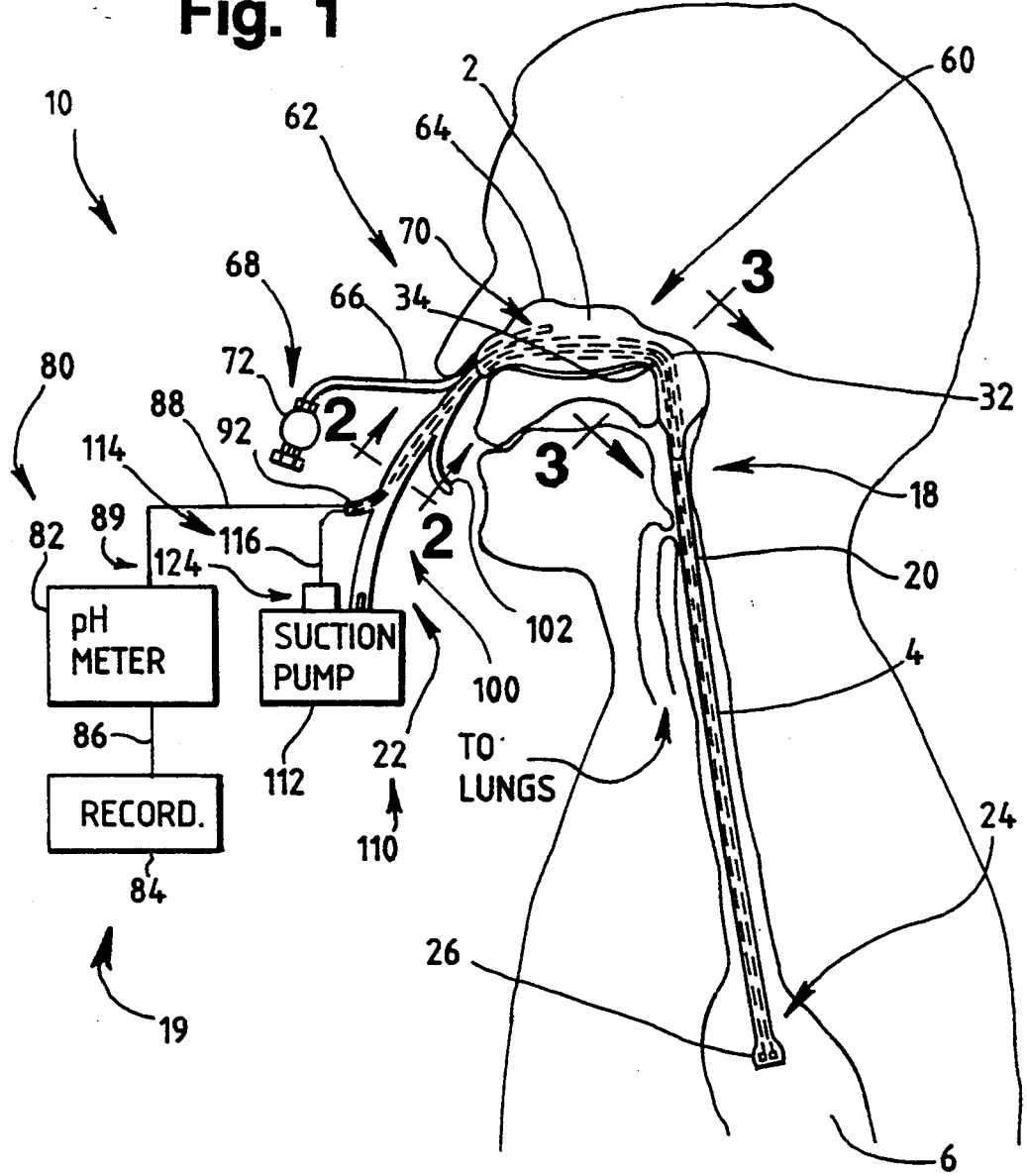
FIG. 1 is a diagrammatic view of a continuous pH monitoring system which is constructed in accordance with the present invention.
Figure 1A:
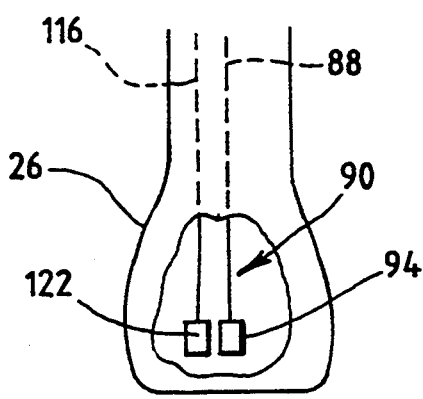
FIG. 1A is an enlarged cut-out view of a distal end of a nasogastric tube of FIG. 1.

Referring now to the drawings, and more particularly to FIGS. 1, 1A, 2 and 3 thereof, there is shown a pH level monitoring system 10 which is constructed in accordance with the present invention. The monitoring system 10 is utilized in patient care for supplying health care workers with information concerning the status of patient pH levels in a relatively easy manner without causing undue discomfort to the patient.

The monitoring system 10 generally includes a nasogastric stomach receiving catheter assembly 18 for providing fluid communication with the stomach 6 of a patient via the nasal cavity 2 and esophagus 4, and a monitoring and aspirating arrangement 19 for determining stomach pH levels and for removing undesired and unwanted stomach fluids from the patient. An anchor assembly 60 attached to the catheter assembly 18 secures it within the nasal cavity 2 to prevent chaffing of the sensitive nasal cavity tissues. For the purpose of equalizing the air pressure within the stomach 6 with the atmospheric air pressure, a vent 100 is provided substantially within the catheter assembly 18.

In operation, the catheter assembly 18 is inserted into the upper region of the stomach 6 via the nasal cavity 2 and esophagus 4. Once the catheter assembly 18 has been disposed in a desired position, with the anchor assembly 60 resting within the nasal cavity 2, a doctor or other health care worker causes air to enter the anchor assembly 60 allowing it to expand, thereby pressing it against the nasal cavity 2. In this way, the catheter assembly 18 is held frictionally in place, preventing the catheter assembly 18 from moving and rubbing the sensitive nasal cavity tissues.

Once the catheter assembly 18 has been properly anchored by the anchor assembly 60, the monitoring and aspirating arrangement 19 is connected to the catheter assembly 18 to enable stomach pH levels to be monitored and to permit unwanted stomach fluids to be removed. The vent 100 provides fluid communication between the atmosphere and the stomach 6 to prevent excessive negative pressure from developing in the stomach 6 of the patient. From the foregoing, it should be understood the arrangement 19 is able to measure and record the pH level of the patient continuously, for substantial periods of time.

Considering now the catheter assembly 18 in greater detail with reference to FIGS. 1, 1A, 2 and 3, the catheter assembly 18 generally includes an elongated tube 20 which is sized to permit comfortable insertion into the nasal cavity 2. The tube 20 is preferably made of a flexible thermoplastic material to aid in conforming to the contours of the nasogastric tract between the nasal cavity 2 and the stomach 6. In addition, the tube 20 is compressible, so that when bent, it changes from a substantially circular shape in cross-section to a somewhat elliptical shape in cross-section. In this regard, the tube 20 may be easily bent at about 90 degrees between the nasal cavity 2 and the entrance to esophagus 4, thus making insertion less uncomfortable.

Also to make insertion into the stomach less uncomfortable, a distal end portion 24 of the tube has a somewhat bulbous rounded tip 26. Such a bulbous shape permits insertion of the tube 20 into the nasal cavity 2 and down the esophagus 4 with minimal abrasion of the sensitive tissues within the nasogastric tract. As best seen in FIG. 1, when the catheter assembly 18 is fully inserted, the distal end 24 rests within the stomach 6, while a proximal end 22 of the tube 20 extends outside of the patient via the nasal passageway. In this way, instrumentation like the monitoring and aspirating arrangement 19 may be connected electrically and mechanically through the proximal end 22 of the tube 20.

Considering now the monitoring and aspirating arrangement 19 in greater detail with reference to FIG. 1, the monitoring and aspirating arrangement 19 generally includes a readout or indicator assembly 80 for providing visual readout information regarding the stomach pH levels and an aspirating assembly 110 for removing unwanted stomach fluids from the patient.

Considering now the anchor assembly 60 in greater detail with reference to FIG. 1, the anchor assembly 60 includes an inflatable cuff assembly 62 having a balloon 64 attached circumferentially to the exterior surface 36 (FIGS. 2 and 3) of tube 20 and positioned such that when the tube 20 is inserted fully, the balloon 64 is located within the nasal cavity 2.

Located outside of the tube 20 is an inflation member 66 having a proximal end 68 and a distal end 70. Distal end 70 terminates within the balloon 64 and proximal end 68 extends outside of the balloon 64 to provide an air passage for inflating the balloon 64. In this way, the circumference of the tube 20 is not increased to accommodate another passageway for inflation of the balloon 64. A pump device 72 is connected to the inflation member proximal end 68 to expand the balloon 64 within the nasal cavity 2 to secure the tube 20.

In operation, the inflatable cuff assembly 62 is positioned within the nasal cavity 2 when the catheter assembly 18 is fully inserted. The balloon 64 is then inflated using the pump device 72, such as a manually activated squeeze type pump, until the balloon 64 has expanded, filling the void between the exterior surface 36 and the nasal cavity 2, the catheter assembly 18 is thus secured within the nasal cavity 2, restricting any movement of the tube 20.

Figure 2:
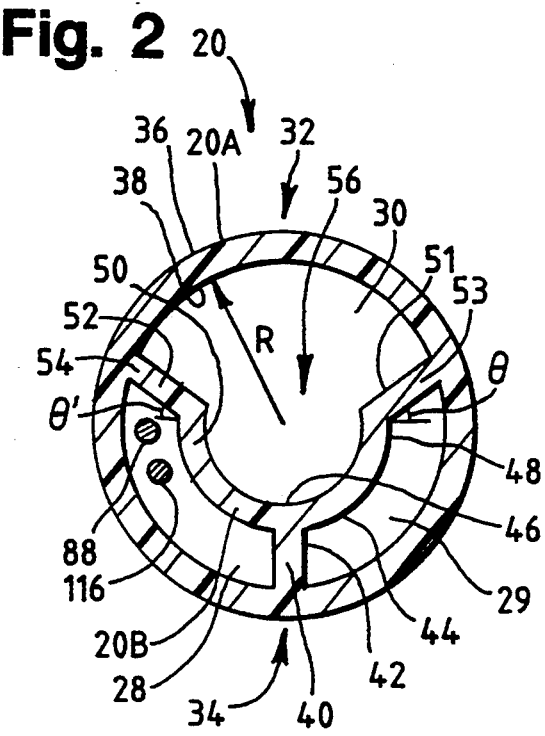
FIG. 2 is a cross-section of the nasogastric tube of FIG. 1 taken along line 2—2 illustrating the tube in a non-compressed state.
Figure 3:
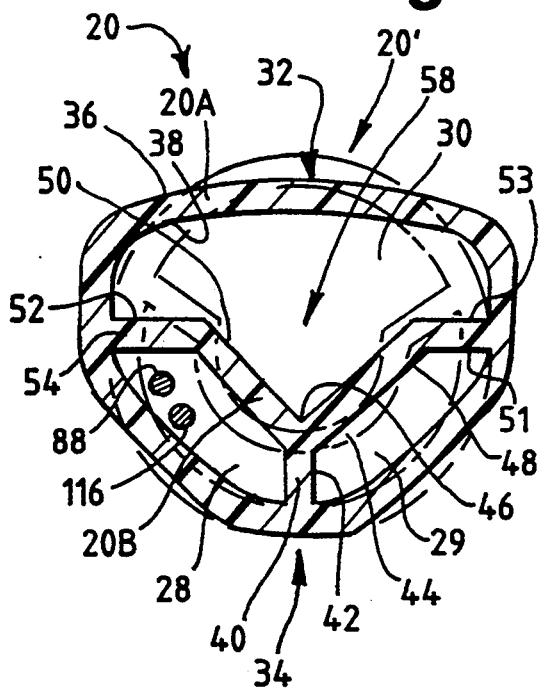
FIG. 3 is a cross-section of the nasogastric tube of FIG. 1 taken along line 3—3 illustrating the tube in a compressed state.

Considering now the tube 20 in still greater detail, with reference to FIGS. 2 and 3, the tube 20 generally includes a plurality of coaxial passageways, such as passageways 28-30 for providing a series of spaced apart along the longitudinal length of the tube 20. Although in the preferred embodiment, three passageways (28-30) are utilized, those skilled in the art will understand that more than three passageways may be accommodated within the tube 20.

The passageways 28-30 are defined by an external tube wall 20A which extends around the circumference of the tube 20 and an interior tube wall 20B which is generally Y shaped. Interior wall 20B has a right hand wall portion 48, a left hand wall portion 50 and a central or common wall portion 40 for dividing the interior of the tube 20 into the three separate passageways 28-30. As best seen in FIGS. 2 and 3, external tube wall 20A has an interior wall surface 38 and an exterior wall surface 36. Attached integrally to the interior wall surface 38, and aligned coaxially with the tube 20, is the common wall 40. Common wall 40 extends radially inwardly toward the center of the tube 20 between about one quarter and about one half of the radius R of tube 20 terminating at a distal end 42. The common wall 40 separates passageways 28 and 29 from one another to permit them to perform separate functions without interference with one another.

The common wall distal end 42 is integrally connected at a midpoint 46 to both the right hand wall portion 48, and the left hand wall portion 50. The right hand wall portion 48 and left hand wall portion 50 are spaced apart from the exterior wall surface 36 and define a resilient inner wall member 44. The right hand wall portion 48 and the left hand wall portion 50 include a pair of end walls 51 and 52, respectively. End walls 51 and 52, extend radially outwardly from the right hand wall 48 and the left hand wall portion 50, respectively, at an angle $\theta$ and $\theta^1$, respectively, from the horizontal plane terminating at opposite distal ends 53 and 54 respectively. Opposite distal ends 53 and 54 attach integrally to the interior wall surface 38 to separate passageway 28 from passageway 30 and passageway 29 from passageway 30, respectively. In this regard, passageways 28 and 29 are substantially equal in size and both are smaller than passageway 30.

As best seen in FIGS. 1-3, the tube 20 makes a number of direction changes along its path into the stomach 6, each of which causes the tube 20 to be deformed. These deformations of the tube 20 range from substantially a non-stressed or zero deformation state at a straight portion of the tube, such as illustrated in FIG. 2, to a substantially stressed large deformation state at a 90 degree bend, such as illustrated in FIG. 3.

Considering now the stressed state of the tube 20, with reference to FIGS. 2 and 3, tube 20 has a lower portion 34 and an upper portion 32 which are subject to deformation due to bending of the tube 20. In this regard, in a stationary position, tube 20 is configured so that the upper portion 32 forms the outer radius of the 90 degree bend and the lower portion 34 forms the inner radius of the 90 degree bend.

As best seen in FIG. 2, the tube 20 is substantially in a noncompressed state. Upper portion 32 and lower portion 34 are substantially arcuate and angles $\theta$ and $\theta^1$ are each between about 10 and about 80 degrees. The inner wall 46 forms a substantially U-shaped channel which is approximately concentric with the exterior wall surface 36 in this noncompressed state.

As best seen in FIG. 3, when the tube 20 is placed in a substantially compressed state, the tube 20 is subject to deformation. Tube 20' is illustrative of tube 20 in a precompressed state and shows the changes undergone by tube 20. In this regard, as tube 20 is bent, through 90 degrees, the upper portion 32 flattens out while the lower portion 34 only partially flattens, remaining substantially arcuate in the area adjacent to the common wall 40. While upper and lower portions 32, 34 are undergoing the flattening process, tube 20 becomes thinner along its vertical axis while simultaneously becoming wider along its horizontal axis.

As a result of the flattening of upper and lower portions 32, 34, the end walls 51 and 52 are flexed about their respective opposite distal ends 53, 54 towards the upper portion 32, deforming the resilient wall 44 into substantially a V-shape. As end walls 51 and 52 are flexed downwardly, angles $\theta$ and $\theta^1$ are reduced to substantially 0 degrees. In this way, that portion of exterior wall surface 36 which contacts the nasal cavity 2 is increased, thus causing the flattened tube 20 to exert a force no more than that of a round tube, such as tube 20' but distributed over a substantially wider contact area. Thus, the concentration of force is reduced by such distribution to cause the level of discomfort experienced by the patient to be reduced substantially.

Considering now the indicator assembly 80 in greater detail with respect to FIGS. 1-3, indicator assembly 80 generally includes a meter device 82 to measure stomach fluid pH levels and a sensor device 94 located within the tube distal end 24 to produce electrical signals indicative of pH levels. The meter 82 is electrically connected to the sensor 94 by an electrical conductor 88 which is disposed substantially within one of the tube passageways, such as the passageway 28.

Indicator assembly 80 also includes a recording device 84 electrically connected to the meter device 82 for providing print out measurement readings made by the meter device 82. Device 84 thus enables pH information to be recorded continuously.

An instrument pigtail 92 provides access to passageway 28 and penetrates the exterior and interior wall surfaces 36, 38 respectively at the proximal end 22 portion of tube 20 terminating therein. In this regard, the pigtail 92 provides an extension of passageway 28 beyond the exterior wall surface 36 to aid in the insertion of conductors and sensor devices, such as conductor 88 and sensor device 94, into passageway 28. It should be noted that although the use of a pigtail, such as pigtail 92, is preferred, access to passageway 28 may also be achieved by providing an opening through exterior and interior wall surfaces 36 and 38 to passageway 28.

In operation, after tube 20 is properly positioned, the sensor device 94 located in the tube's distal end 24 makes contact with fluids within the stomach 6. Upon making contact with the stomach fluids, sensor 94 transmits an electrical signal via conductor 88 to the meter device 82. The transmitted electrical signal is indicative of the stomach pH levels. Continuous monitoring, even with no health care workers present, is accomplished by way of the recording device 84, via conductor 86, which registers the pH level in a permanent record.

The meter device 82 is capable of visually indicating pH levels measured by sensor device 94. Such a meter device 82 is manufactured by Sentron Incorporated of Federal Way, Washington.

During use, the meter device 82 receives electrical signals from sensor device 94 and displays the pH level representative of the electrical signals received.

Sensor device 94 is hydrogen ion sensitive, such as the ISFET sensor used in the SENTRON 1001 manufactured by Sentron Incorporated of Federal Way, Wash., and is capable of producing an electric signal representative of the pH level of a substance in contact with the sensor 94.

In operation, the sensor device 94 contacts fluid within the stomach 6. When the hydrogen ion concentration in the fluid varies, electrical current flow through sensor device 94 changes, altering the electrical signal delivered to the meter device 82 by the sensor device 94 through the conductor 88. The meter device 82 then converts the electrical signal into a pH level reading.

Considering now the vent 100 in greater detail with respect to FIGS. 1, 1A, 2 and 3, vent 100 includes a passageway, such as passageway 29, for supplying atmospheric air to the stomach 6. In this way, the air pressure within the stomach 6 can be adjusted to be about equal with the atmospheric air pressure.

Vent 100 also includes a vent pigtail 102 connected integrally to passageway 29 near the tube proximal end 22. Vent pigtail 102 is similar in construction to pigtail 92 and, therefore, will not be described in further detail.

Considering now the aspirating assembly 110 in greater detail with FIGS. 1, 1A, 2 and 3, the aspirating assembly 110 generally includes a suction pump device 112 to aspirate stomach fluid as required via the passageway 30. A switch device 124 controls the pump 112. The switch device 124 is connected electrically to the pump 112 via an electrical conductor 116 which is disposed substantially within passageway 28. A pressure sensing device 122 located within the tube distal end 24 produces electrical signals indicative of the pressure within the stomach 6. Such signals are transmitted via the conductor 116 to the switch device 124 for controlling the operation of the suction pump device 112.

The suction pump device 112 operates periodically to remove unwanted and undesired fluids from the stomach 6. In this regard, both activation and deactivation of the device 112 is scheduled. During activation periods, the suction pump device 112 is activated, aspirating the stomach 6. During activation of the pump 112 and prior to the scheduled shut off time, the sensing device 122 may detect a predetermined stomach negative pressure level, causing the suction pump device 112 to be deactivated prior to the scheduled shut off time.

During scheduled activation, the suction pump device 112 creates a vacuum in passageway 30 between the suction pump device 112 and the tube distal end 24. In this regard, the vacuum causes fluids in the stomach 6 to be drawn into passageway 30 and thence up through the tube 20 and into the suction pump device 112 for discharge purposes.

Considering now the pressure sensing device 122 in greater detail, the pressure sensing device 122 is a transducer device which converts pressure measurements into an electrical signals. Such a device is sized to fit within one of the passageways, such as the passageway 28, and is capable of being submersed completely in stomach fluid without any adverse affects.

In operation, pressure sensing device 122 detects pressure within the stomach 6 during operation of the suction pump device 112 by converting a sensed pressure into an electrical signal representative of the stomach pressure. The output electrical signal from the device 122 is then conducted to the switch device 124 through the conductor 116. In this regard, when the electrical signal is indicative that a predetermined negative pressure state exists in the stomach 6, the switch device 124 causes the suction pump device 112 to be turned off. Removing such a negative pressure assures the distal end 24 of the tube 20 is prevented from being contorted by pressure differences to cause the distal end 24 to contact the stomach wall. Thus, injury to the patient is prevented.

Figure 4:
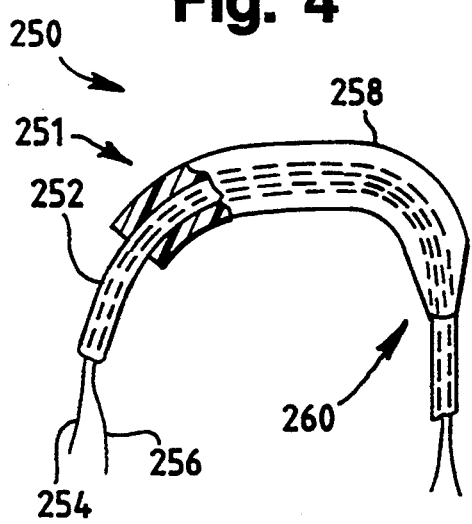
FIG. 4 is an elevational view of an alternative embodiment of an anchor assembly.

Referring now to FIG. 4 there is shown another pH level monitoring system 250 which is constructed in accordance to the present invention. The system 250 is substantially similar to system 10 except that it includes an alternative embodiment anchor assembly 251.

Considering now the anchor assembly 251 in greater detail with reference to FIG. 4, the anchor assembly 251 is similar to anchor assembly 60 except that it employs a resilient sponge member 258 instead of an inflatable cuff assembly 62. The sponge member 258 is generally composed of a dense material having a sufficient density to contract when compressed and sufficiently resilient to expand to its original shape after the compressive force is removed. The resilient sponge member 258 includes a tapered leading portion 260 attached circumferentially to tube 252 for minimizing contact with internal nasal cavity tissue during insertion of the anchor assembly 251.

In operation, sponge member 258 is compressed prior to insertion of anchor assembly 250 into the nasal cavity 2. The tube 252 is then urged further into the nasogastric tract until the tube 252 is fully inserted to its desired position. Once in place, the sponge member 258 expands, filling the void between the tube 252 and the nasal cavity 2. The outwardly expanding sponge member 258 contacts the surface of the nasal cavity 2 and secures frictionally the tube 252 in position.

Figure 6:
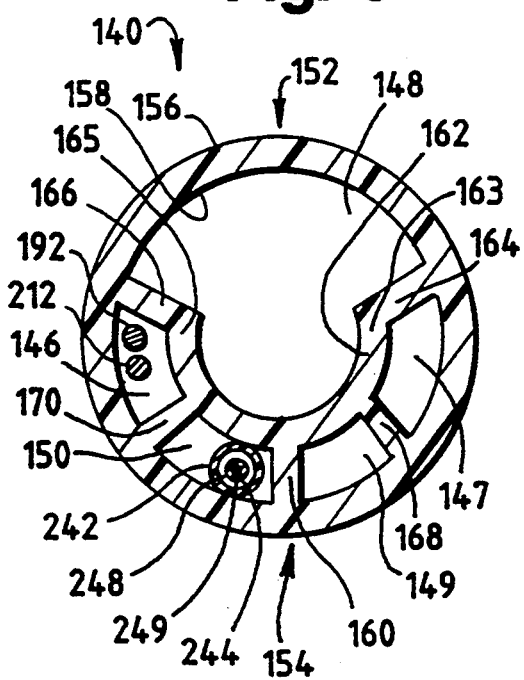
FIG. 6 is a cross-section of a nasogastric tube taken along line 6—6 of FIG. 5.
Figure 5:
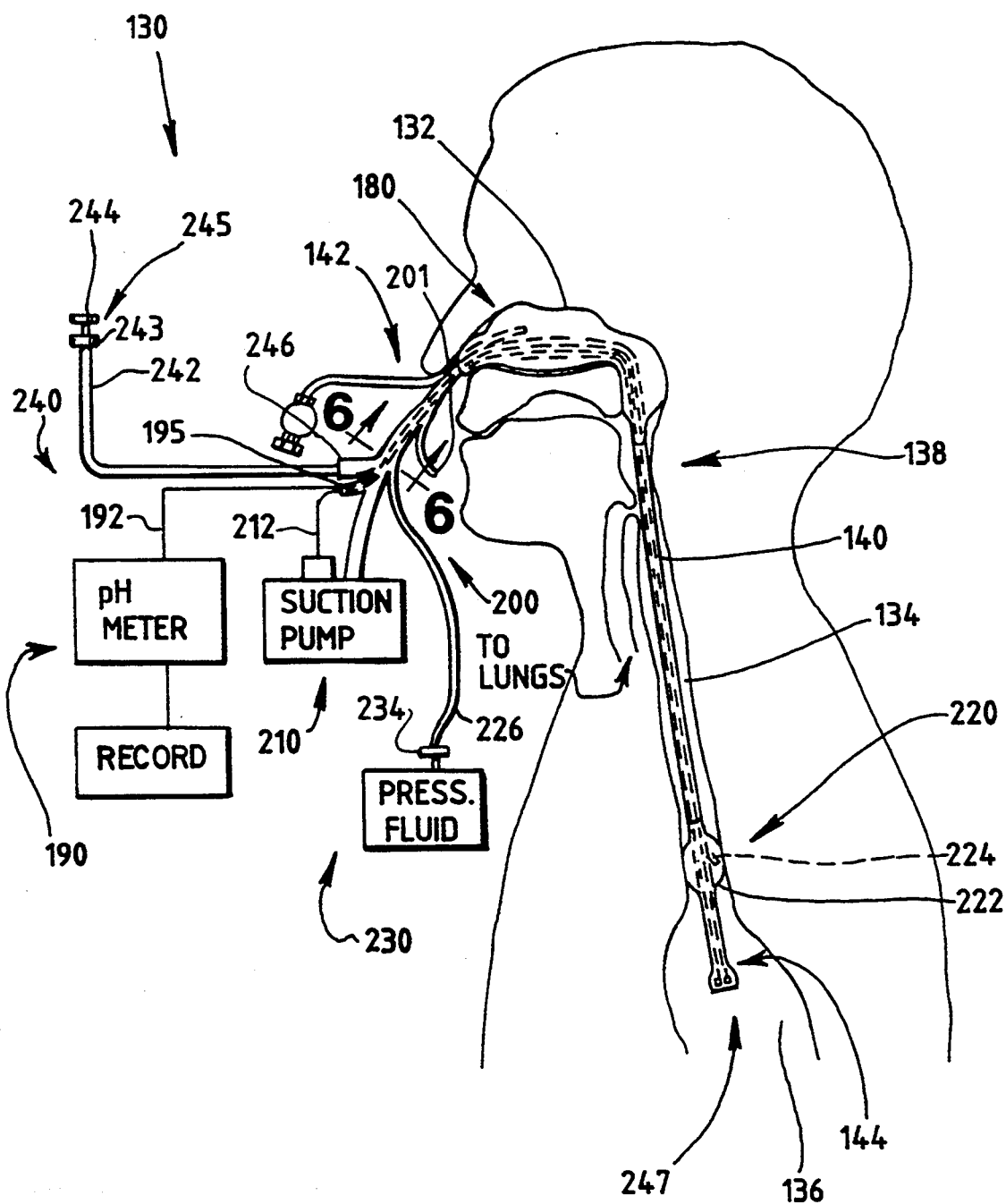
FIG. 5 is a diagrammatical view of another monitoring system which is constructed in accordance with the present invention.

Referring now to FIGS. 5 and 6, there is shown an alternative embodiment of a monitoring system 130 which is constructed in accordance with the present invention. Monitoring system 130 is similar to monitoring system 10 with certain exceptions which will be described hereinafter in greater detail.

As best seen in FIG. 5, monitoring system 130 further includes a lower anchor assembly 220 attached to a catheter assembly 138 to secure it and prevent it from contacting sensitive interior surfaces of the stomach 136, and a feeding tube assembly 240 contained substantially within catheter assembly 138 to access the stomach 136 extracorporeally for providing nourishment or medication to the patient.

In use, monitoring system 130 operates in substantially the same manner as monitoring system 10. Catheter assembly 138 is first inserted into the patient. Lower anchor assembly 220 is then expanded, bracing the catheter assembly 138 near the stomach 136. Once the catheter assembly 130 is secured, feeding tube assembly 240 is inserted into catheter assembly 138 and nourishing foodstuffs or medications are supplied to the stomach 136.

Considering now catheter assembly 138 in greater detail with reference to FIGS. 5 and 6, catheter assembly 138 generally includes an elongated tube 140 having a proximal end 142 and a distal end 144. Tube 140 is similar to tube 20 and may be constructed of similar materials. Thus, tube 140 is flexible and compressible as is tube 20. As best seen in FIG. 5, when catheter assembly 138 is fully inserted, distal end 144 rests within the stomach 136 while proximal end 142 extends outside of the patient.

Considering now the lower anchor assembly 220 in greater detail with reference to FIGS. 5 and 6, lower anchor assembly 220 includes a balloon member 222 similar in construction to balloon 64, an inflation member 224 which extends from tube 140 to the interior of balloon member 222 to permit air transmission from tube 140 to the balloon member 222, a pigtail 226 connected integrally to proximal end 142 and having an engagement member 234 to connect a source of pressurized fluid to lower anchor assembly 220, and an insufflation assembly 230 connected releasably to engagement member 234 to supply a pressurized source of air.

In operation, insufflation assembly 230 engages engagement member 234 to initiate the flow of pressurized air into pigtail 226, through tube 140 and inflation member 224 into the balloon member 222. Balloon member 222 is then expanded, filling the void between the tube 140 and the esophagus 134 to secure the tube distal end 220. Once balloon member 222 is fully inflated, insufflation assembly 230 is disengaged from engagement member 234, thereby ceasing expansion of the balloon member 222.

To enhance the safety of using the balloon device 222, the insufflation assembly 230 includes a pressure relieving device, such as a spring loaded pop valve (not shown). It will be understood by one skilled in the art that such a pressure relieving device may also be used in conjunction with the anchor assembly 60 to prevent excessive pressure accumulation.

Considering now the feeding tube assembly 240 in greater detail with reference to FIGS. 5 and 6, feeding tube assembly 240 includes a semi-rigid sheath member 242 having an insertion end member 243 and contained removably within the tube 140 and an inner tube member 244 having a proximal end 245 and a distal end 247 and contained removably within sheath member 242 to provide a passageway between a source (not shown) of nourishment or medication outside of the patient's body and the stomach 136.

In operation, sheath member 242 is inserted into tube 140. It will be understood by one skilled in the art that the distance of insertion will vary according to the physical requirements of the patient. The inner tube member 244 is then inserted into an opening (not shown) in the insertion end member 243 until distal end 247 is positioned adjacent to the stomach 136. Nourishing matter is then passed through inner tube member 244 to the stomach as required. It will be understood by one skilled in the art that the feeding tube assembly 240 may also be used to supply medication to the stomach 136 in a similar manner.

Considering now the tube 140 in greater detail with reference to FIG. 6, the tube 140 generally includes a plurality of passageways, such as passageways 146–150, for providing spaced apart passageways between proximal end 142 and distal end 144.

Tube 140 includes an external tube wall 140A having exterior wall and interior wall surfaces 156 and 158, an internal radial barrier 160 attached integrally to the interior wall surface 158, a resilient inner wall member 162 having a right hand distal end 163 and a left hand distal end 165 and spaced apart from the exterior wall surface 156 and connected at about its midpoint to the internal radial barrier 160, and a pair of end walls 164 and 166 disposed between the right hand distal end 163 and the interior wall surface 158, and the left hand distal end 165 and the interior wall surface 158, respectively, forming passageway 148.

Tube 140 further includes a pair of rib walls 168 and 170 which are coaxial with internal radial barrier 160 and are attached integrally between the interior wall surface 158 and the resilient inner wall member 162. Rib wall 168 is fixed between internal radial barrier 160 and end wall 164 forming passageways 147 and 149. Rib wall 170 is fixed between internal radial barrier 160 and end wall 166 forming passageways 146 and 150.

Rib walls 168 and 170 support resilient inner wall member 162 and further reduce the possibility of passageways 146, 147, 149 and 150 being closed off due to forces exerted on the tube 140, such as when tube 140 is put through a 90 degree bend. This is especially important where a passageway is utilized as a return air vent where its blockage would interrupt normal operation of the monitor system 130.

Tube 140 further includes a plurality of pigtails, such as pigtails 195, 201, 226 and 246, extending from the proximal end 142 and providing access to passageways 146, 147, 149 and 150 respectively. Each pigtail 195, 201, 226 and 246 penetrates the tubes exterior wall surface 156 and interior wall surface 158 and terminates in the respective passageway, thereby extending the passageways 146, 147, 149 and 150 outside the perimeter of the tube 140.

Considering now sheath member 242 in greater detail with reference to FIGS. 5 and 6, sheath member 242 is cylindrical, having a wall 242A and an internal shaft 248. Sheath member 242 is made of a thermoplastic material and is somewhat flexible to bend within tube 140 yet is rigid enough to resist internal shaft 248 from being closed off.

Considering now inner tube member 244 in greater detail with reference to FIGS. 5 and 6, inner tube member 244 is cylindrical, having an internal shaft 249, and a wall 244A whose outer diameter sized to fit slidably within internal shaft 248. Inner tube 244 is made of a thermoplastic material and is flexible. When in the desired position, the distal end 247 is adjacent to the stomach 136 for supplying thereto nourishment or medication as required.

While particular embodiments of the present invention have been disclosed, it is to be understood that various different modifications are possible and are contemplated within the true spirit and scope of the appended claims. For example, the feeding tube and electrical conductors can be considered a line, as hereinafter specified in the claims. There is no intention, therefore, of limitations to the exact abstract or disclosure herein presented.

What is claimed is:

1. A monitoring system for use with a pH meter means for monitoring the pH levels in a stomach of a patient and suction means for facilitating withdrawing stomach fluids from the stomach of the patient, comprising:
   a tube device defining at least one internal passageway, having a proximal end and a distal end;
   electrical detecting means disposed at the distal end of said tube device for sensing pH levels in a patient's stomach fluids;
   electrical pressure sensing means disposed at the distal end of said tube device for detecting pressure within a patient's stomach;
   pH meter conductor means disposed within said at least one passageway, for extending from said detecting means to said pH meter means, for carrying pH information to said pH meter means; and
   pressure sensing conductor means disposed within said at least one passageway for extending from said pressure sensing means to the suction means, for conveying a deactivating signal to the suction means for deactivating the suction means when the pressure within the stomach decreases below a predetermined pressure.

2. A monitoring system according to claim 1, further comprising:
   anchor assembly means disposed on a portion of the tube device adapted to be directly adjacent to nasal cavity of a patient for securing said tube device within the nasal cavity of the patient to prevent relative motion between the nasal cavity and said tube device.

3. A system according to claim 2, further including a lower anchor assembly means for securing said distal end to prevent said distal end from contacting a patient's stomach lining, said lower anchor assembly means having a balloon device connected circumferentially to an exterior surface of said tube device and adjacent to said distal end to brace said tube device within a patient's esophagus, a lower inflation member connected integrally to said at least one internal passageway and extending into and terminating within said balloon device to create an air passage between said internal passageway and said balloon device, and compressor means for supplying air under pressure connected integrally to said internal inner passageway at said proximal end of said tube device to inflate said balloon device.

4. A system according to claim 2, further including feeding tube means for introducing nutritional elements into the patient's stomach, said tube means having a sheath member sized and dimensioned to be inserted within said at least one internal passageway and an inner tube sized and dimensioned to be inserted in and removed from said sheath member.

5. A monitoring system according to claim 1, further comprising:
   vent means adapted to be in fluid communication with the stomach of the patient to permit atmospheric air to enter the stomach for equalizing substantially the air pressure within the stomach with atmospheric air pressure.

6. A monitoring system for use with a pH meter means for monitoring the pH level in a stomach of a patient, comprising:
   a tube device having a distal end to be inserted into the stomach of a patient;
   detecting means disposed at said distal end of said tube device for sensing pH levels of fluids within the stomach of the patient;
   pH meter conductor means for extending from said detecting means to said pH meter means, for carrying pH information to said pH meter means;
   anchor assembly means disposed on a portion of the tube device adapted to be directly adjacent to a nasal cavity of the patient for securing said tube device within the nasal cavity to prevent relative motion between the nasal cavity and said tube device; and
   said anchor assembly means is an inflatable cuff assembly, said inflatable cuff assembly including an inflatable balloon device to expand within the nasal cavity of the patient, an inflation member located outside of said tube device having a proximal end and a distal end, said distal end being within said balloon device and said proximal end extending outside of said balloon device to allow inflation of said balloon device, and a pump device connected to said proximal end for permitting expansion of said balloon device.

7. A monitoring system for use with a pH meter means, comprising:
   a tube device having a distal end to be inserted into a stomach of a patient;
   detecting means disposed at said distal end of said tube device for sensing pH levels of fluids within the stomach of the patient;
   pH meter conductor means for extending from said detecting means to said pH meter means, for carrying pH information to said pH meter means;
   anchor assembly means disposed on a portion of the tube device adapted to be directly adjacent to a nasal cavity of the patient for securing said tube device within the nasal cavity to prevent relative motion between the nasal cavity and said tube device; and
   wherein said anchor assembly means is a sponge member, said sponge member being of such density as to contract when compressed for insertion into the nasal cavity and to expand when in place within said nasal cavity to hold frictionally said tube device.

8. A monitoring system for use with a pH meter means for monitoring a pH levels in the stomach of a patient, comprising:
   a tube device having a distal end to be inserted into the stomach of a patient;
   detecting means disposed at said distal end of said tube device for sensing pH levels of fluids within the stomach of the patient;

pH meter conductor means for extending from said detecting means to said pH meter means, for carrying pH information to said pH meter means;

aspirating means for removing fluid from a patient's stomach;

a suction pump device attached to said tube device to cause said fluid from the stomach to be transported extracorporeally; and manometer means for controlling said aspirating means, said manometer means having a sensor device to detect pressure within the stomach of the patient and a switch device connected to said sensor device to stop said aspirating means, to prevent vacuum contacting an inner lining of the stomach, and causing damage to that inner lining.

9. A method for monitoring pH levels of stomach fluids of a patient, comprising:

coupling a tube device having at least one internal passageway to pH meter means for measuring the pH levels of the patient's stomach fluid;

extending conductor means within said at least one passageway of said tube device for carrying pH information to the pH meter means;

inserting said tube device into a patient's stomach;

generating signals indicative of the pH levels of the stomach fluids of the patient;

coupling said signals to said conductor means;

accessing the patient's stomach with a tube device, said tube device being a flexible collapsible tube having a proximal end and a distal end for insertion into a nasal cavity, through an esophagus and into the stomach, said distal end being rounded and bulbous to aid in insertion of said tube;

said tube device also having at least one internal passageway substantially equal in length to said tube for providing separate isolated passageways between said distal end and said proximal end;

securing said tube device within said nasal cavity with an anchor assembly connected circumferentially to an exterior surface of said tube to prevent relative motion between said nasal cavity and said tube;

disposing an electrical conductor substantially within one of said passageways and connected at one end to pressure sensing means to transmit a signal and a pressure detecting device connected at another end of said electrical conductor to produce said signal for indicating the pressure within the stomach;

attaching a recording device to said pH meter means to register pH of fluids within the stomach;

supplying the stomach with atmospheric air through a vent included in said at least one internal passageway for permitting atmospheric air to enter the stomach to equalize substantially air pressure within the stomach with the atmospheric air pressure; and removing fluid from the stomach with an aspirating assembly having a suction pump device attached to said at least one passageway to transport extracorporeally fluid from the stomach.

10. A method according to claim 9, further including securing said distal end with another anchor assembly to prevent said distal end from contacting the stomach, said another anchor assembly having a lower balloon device connected circumferentially to said exterior surface and adjacent to said distal end to brace said tube within said esophagus, a lower inflation member connected integrally to said at least one passageway and extending into and terminating within said lower balloon device to create an air passage between said at least one passageway and said lower balloon device, and compressor means for supplying air under pressure connected integrally to said at least one passageway at said proximal end to inflate said lower balloon device, said step of securing including a step of supplying air to the lower inflation member.

* * * * *